(12) United States Patent
Azad et al.

(10) Patent No.: US 8,222,477 B2
(45) Date of Patent: Jul. 17, 2012

(54) SUPERABSORBENT POLYMER CONTAINING CLAY, PARTICULATE, AND METHOD OF MAKING SAME

(75) Inventors: Michael M. Azad, Reidsville, NC (US); Scott J. Smith, Greensboro, NC (US); Mark Joy, Reidsville, NC (US); Geoffrey Wyatt Blake, Kernersville, NC (US); Michael S. Jarman, High Point, NC (US)

(73) Assignee: Evonik Stockhausen, LLC, Greensboro, NC (US)

( * ) Notice: Subject to any disclaimer, the term of this patent is extended or adjusted under 35 U.S.C. 154(b) by 494 days.

(21) Appl. No.: 12/254,434

(22) Filed: Oct. 20, 2008

(65) Prior Publication Data

US 2010/0100066 A1   Apr. 22, 2010

(51) Int. Cl.
  *A61F 13/15* (2006.01)
(52) U.S. Cl. .......... 604/372; 604/367; 604/358
(58) Field of Classification Search .......... 604/372
  See application file for complete search history.

(56) References Cited

U.S. PATENT DOCUMENTS

| | | | |
|---|---|---|---|
| 2,531,427 A | | 11/1950 | Hauser |
| 4,286,082 A | | 8/1981 | Tsubakimoto et al. |
| 4,734,478 A | | 3/1988 | Tsubakimoto et al. |
| 5,140,076 A | | 8/1992 | Hatsuda et al. |
| 5,451,613 A | | 9/1995 | Smith et al. |
| 5,462,972 A | | 10/1995 | Smith et al. |
| 5,514,754 A | | 5/1996 | Henderson et al. |
| 5,733,576 A | | 3/1998 | Chmelir |
| 6,124,391 A | * | 9/2000 | Sun et al. ............... 524/447 |
| 6,323,252 B1 | | 11/2001 | Gartner et al. |
| 6,906,131 B2 | | 6/2005 | Ahmed et al. |
| 7,108,916 B2 | * | 9/2006 | Ehrnsperger et al. ......... 428/403 |
| 7,163,966 B2 | | 1/2007 | Joy et al. |

(Continued)

FOREIGN PATENT DOCUMENTS

CA   2460152   10/2009

(Continued)

OTHER PUBLICATIONS

H. Hosseinzadeh et al., Synthesis, Characterization and Swelling Behavior of Gelatin-g-poly(sodium acrylate)/ Kaolin Superabsorbent Hydrogel Composites, copyright 2007, pp. 2057-2069, Journal of Composite Materials, vol. 41, No. 17.

(Continued)

*Primary Examiner* — Lynne Anderson
*Assistant Examiner* — Bradley Philips
(74) *Attorney, Agent, or Firm* — Smith Moore Leatherwood LLP; Philip P. McCann

(57) ABSTRACT

A process for the preparation of superabsorbent polymer containing clay, the process including the steps of (I) polymerizing a polymerization mixture comprising: (a) one or more ethylenically unsaturated carboxyl-containing monomers, (b) one or more crosslinking agents, (c) optionally one or more comonomers copolymerizable with the carboxyl-containing monomer, (d) neutralizing agent to partially neutralize the polymer to from about 50% to about 99%, by weight, and (e) a polymerization medium, to form a crosslinked partially neutralized hydrogel, (II) admixing a clay with the crosslinked partially neutralized hydrogel to form partially neutralized superabsorbent polymer-clay hydrogel; (III) drying the crosslinked partially neutralized hydrogel at a temperature from about 190° C. to about 210° C. and for a time period of from about 15 minutes to about 120 minutes, and (IV) comminuting the dried partially neutralized superabsorbent polymer-clay hydrogel to particles.

17 Claims, 4 Drawing Sheets

U.S. PATENT DOCUMENTS

| | | | |
|---|---|---|---|
| 7,163,969 B2 | 1/2007 | Ahmed et al. | |
| 7,169,843 B2 | 1/2007 | Smith et al. | |
| 7,173,086 B2 * | 2/2007 | Smith et al. | 524/556 |
| 7,239,701 B1 | 7/2007 | Ogishi et al. | |
| 7,241,820 B2 | 7/2007 | Smith et al. | |
| 7,291,674 B2 | 11/2007 | Kang et al. | |
| 7,312,286 B2 | 12/2007 | Lang et al. | |
| 7,335,713 B2 | 2/2008 | Lang et al. | |
| 7,396,584 B2 * | 7/2008 | Azad et al. | 428/327 |
| 7,399,813 B2 | 7/2008 | Lang et al. | |
| 7,427,650 B2 | 9/2008 | Smith et al. | |
| 7,482,058 B2 | 1/2009 | Ahmed et al. | |
| 7,488,541 B2 | 2/2009 | Ahmed et al. | |
| 7,579,402 B2 | 8/2009 | Ahmed et al. | |
| 7,615,579 B2 | 11/2009 | Joy et al. | |
| 7,696,401 B2 | 4/2010 | Qin et al. | |
| 7,777,093 B2 | 8/2010 | Smith et al. | |
| 7,795,345 B2 | 9/2010 | Smith et al. | |
| 7,812,082 B2 | 10/2010 | McIntosh et al. | |
| 7,816,426 B2 | 10/2010 | Ahmed et al. | |
| 7,842,386 B2 | 11/2010 | Loeker et al. | |
| 7,910,688 B2 | 3/2011 | Tian et al. | |
| 2006/0173431 A1 * | 8/2006 | Laumer et al. | 604/372 |
| 2008/0009616 A1 | 1/2008 | Frank et al. | |
| 2008/0234420 A1 | 9/2008 | Smith et al. | |
| 2009/0134357 A1 | 5/2009 | Bub et al. | |
| 2009/0191408 A1 | 7/2009 | Tian et al. | |
| 2010/0075844 A1 | 3/2010 | Loeker et al. | |
| 2010/0130355 A1 | 5/2010 | Tian et al. | |
| 2010/0279860 A1 | 11/2010 | Smith et al. | |
| 2010/0311578 A1 | 12/2010 | Smith et al. | |
| 2011/0009841 A1 | 1/2011 | Ahmed et al. | |
| 2011/0015601 A1 | 1/2011 | Loeker et al. | |
| 2011/0121231 A1 | 5/2011 | Tian et al. | |

FOREIGN PATENT DOCUMENTS

| | | |
|---|---|---|
| CN | 02819951 | 8/2007 |
| EP | 1438354 A1 | 7/2004 |
| GB | 2082614 | 3/1982 |
| WO | 0010619 A1 | 3/2000 |
| WO | 01/68156 A1 | 9/2001 |
| WO | 03025054 A1 | 3/2003 |
| WO | 2010046265 A1 | 4/2010 |

OTHER PUBLICATIONS

International Preliminary Report on Patentability issued on Apr. 26, 2011 in PCT/EP2009/063300.

International Search Report mailed on Feb. 15, 2010 in PCT/EP2009/063300.

Shi et al., U.S. Appl. No. 13/091,844, filed Apr. 21, 2011.

Written Opinion mailed on Feb. 15, 2010 in PCT/EP2009/063300.

* cited by examiner

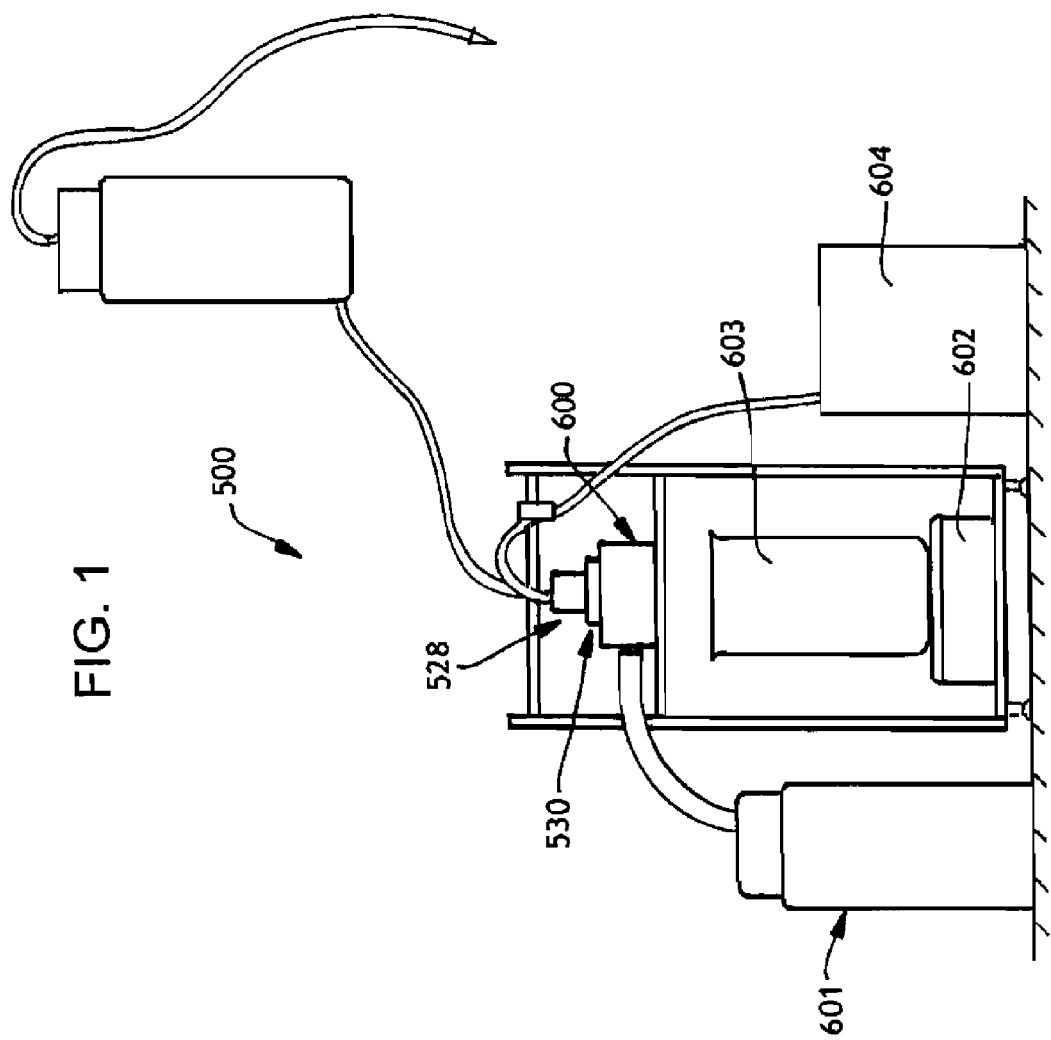

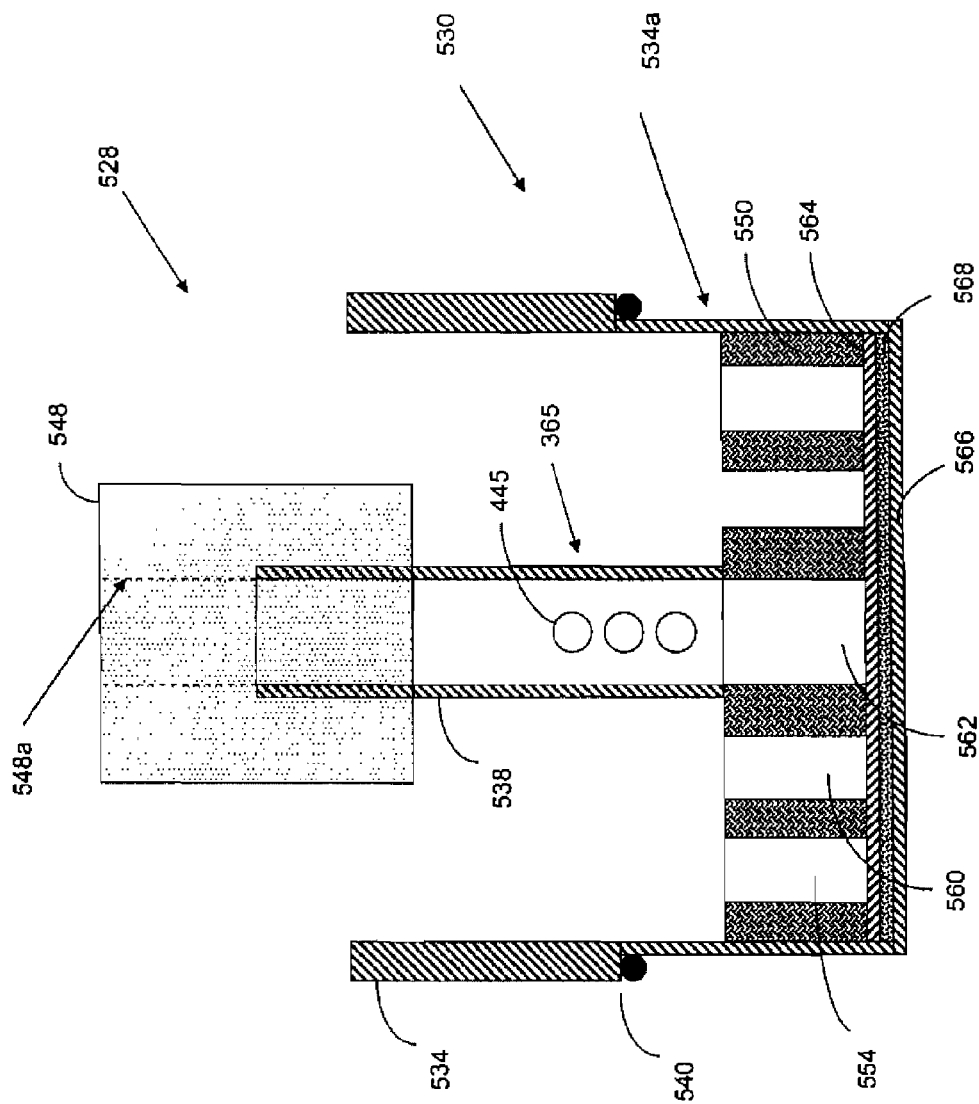

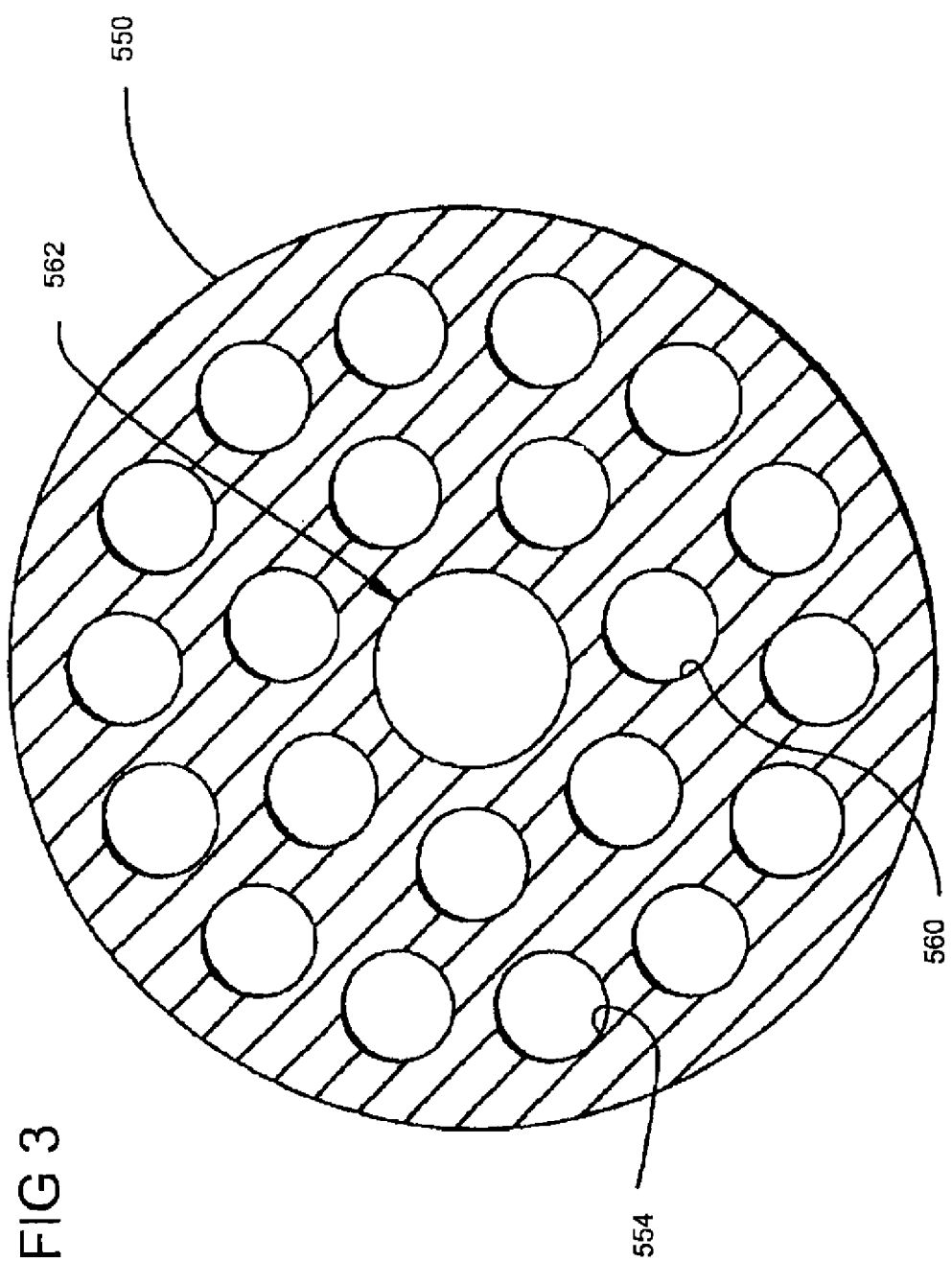

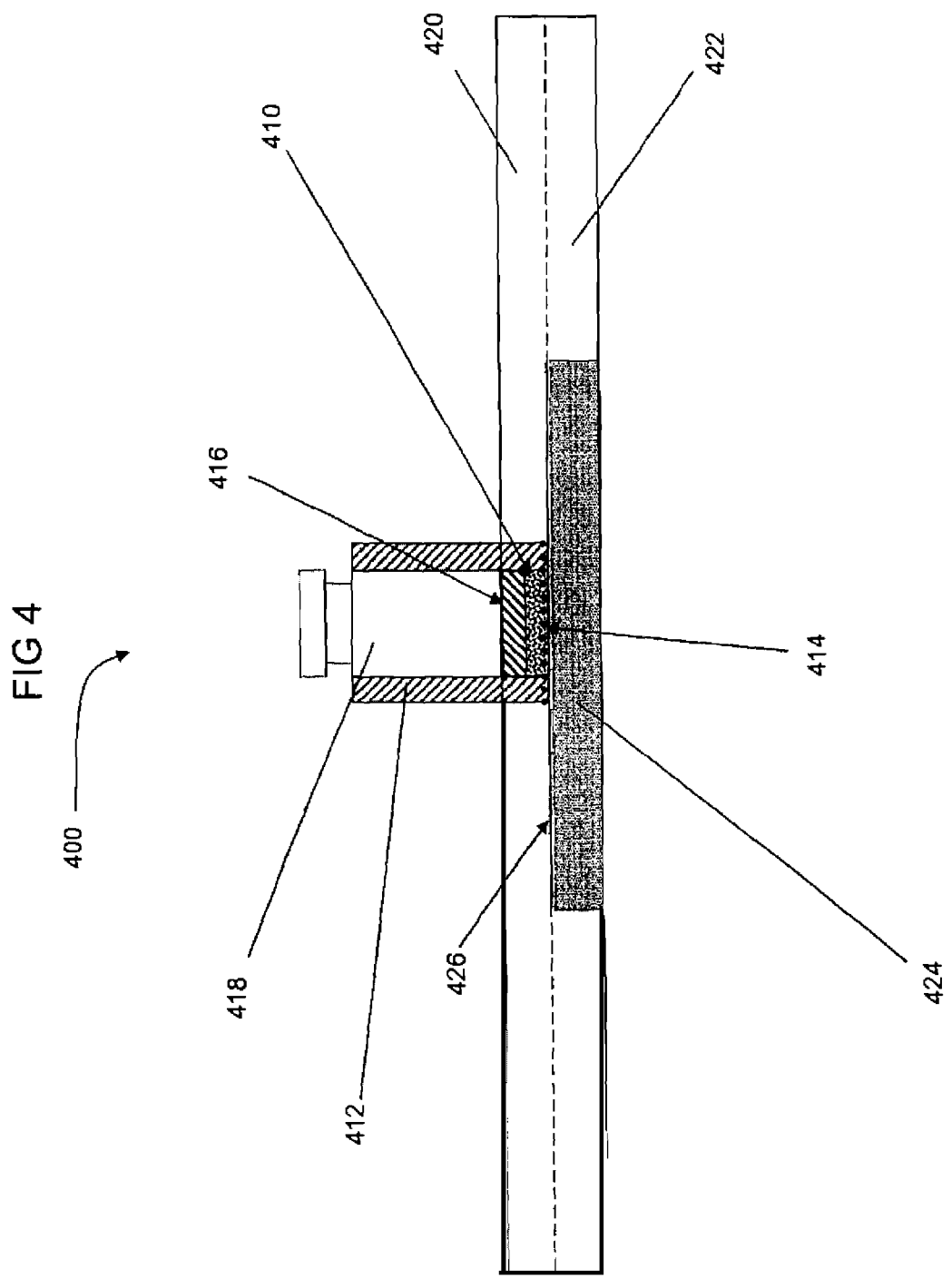

SUPERABSORBENT POLYMER CONTAINING CLAY, PARTICULATE, AND METHOD OF MAKING SAME

BACKGROUND

A superabsorbent material in general refers to a water-swellable, water-insoluble, material capable of absorbing at least about 10 times its weight, and up to about 30 times or more its weight in an aqueous solution containing 0.9 weight percent sodium chloride solution in water. The present invention relates to superabsorbent polymer particles, which absorb water, aqueous liquids, and blood, and a method to make the superabsorbent polymer and particles. The acronym SAP, as used herein and as generally used in the industry, is used in place of superabsorbent polymer, superabsorbent polymer composition, superabsorbent polymer particles, or variations thereof.

A superabsorbent polymer is a cross linked partially neutralized polymer that is capable of absorbing large amounts of aqueous liquids and body fluids, such as urine or blood, with swelling and the formation of hydrogels, and of retaining them under a certain pressure in accordance with the general definition of superabsorbent material. A superabsorbent polymer composition is a superabsorbent polymer that has been surface treated that may include surface cross linking and/or other treatment of the surface of the superabsorbent polymer.

Commercially available superabsorbent polymer compositions include cross linked polyacrylic acids or cross linked starch-acrylic acid graft polymers, in which some of the carboxyl groups are neutralized with sodium hydroxide solution or potassium hydroxide solution. Superabsorbent polymer composition particles are particles of superabsorbent polymers or superabsorbent polymer compositions, and generally have a particle size of from about 150 microns to about 850 mircrons. A comprehensive survey of superabsorbent polymers, and their use and manufacture, is given in F. L. Buchholz and A. T. Graham (editors) in "Modern Superabsorbent Polymer Technology," Wiley-VCH, New York, 1998.

A primary use of SAP and SAP particles is in sanitary articles, such as babies' diapers, incontinence products, or sanitary towels. For fit, comfort, and aesthetic reasons, and from environmental aspects, there is an increasing trend to make sanitary articles smaller and thinner. This is being accomplished by reducing the content of the high volume fluff fiber in these articles. To ensure a constant total retention capacity of body fluids in the sanitary articles, more SAP content is being used in these sanitary articles.

Clays and other mineral products have been added to SAPs in an attempt to improve SAP performance. For example, the addition of finely divided amorphous silica, such as AEROSIL®, available from Evonik GmbH, Germany, or CAB-O-SIL®, available from Cabot Corporation, or a bentonite onto the surface of SAP powders or granules is known. U.S. Pat. Nos. 5,140,076 and 4,734,478 disclose the addition of silica during surface crosslinking of dry SAP powders. U.S. Pat. No. 4,286,082 discloses mixtures of silica and SAP for use in hygiene articles.

Generally, in mixtures of dry SAP particles with a silica powder, the silica adheres to the SAP particle surfaces and alters the surface properties of the SAP particles, but not their intrinsic absorption properties. For example, the silica powder is hydrophilic or hydrophobic, which primarily influences the rate at which a fluid is absorbed by the SAP particles.

Other patents and applications disclosing SAP particles and a clay include GB 2,082,614 disclosing a dry, solid, water-swellable absorbent composition prepared by blending dry SAP particles and 1% to 75%, by weight of the blend, of an extender material selected from uncrosslinked cellulose derivatives, starch, certain clays and minerals, and mixtures thereof.

U.S. Pat. No. 5,733,576 discloses a process of producing absorbing agents containing (a) a water-swellable, synthetic polymer or copolymer, and (b) a natural or synthetic polymeric compound which at normal temperature is a pourable powder and is partially soluble or insoluble in water. The absorbing agents may contain clay as a neutral filling agent.

WO 01/68156 discloses a hydrophilic swellable hydrogel-forming polymer containing alumosilicate and having enhanced permeability and improved odor-control properties. The alumosilicates can be added before, during, or after polymerization.

U.S. Pat. No. 7,329,701 discloses superabsorbent polymer particles containing a clay, wherein the clay is added to an SAP hydrogel prior to SAP neutralization to provide particles having improved fluid acquisition rates and an improved permeability of a fluid through the swollen SAP-clay particles.

The present invention is directed to improving the properties of SAP particles by introducing clay into the SAP hydrogel under specific conditions. It has been found that the addition of clay to a partially neutralized SAP hydrogel and drying the hydrogel-clay at elevated temperatures can improve SAP performance properties. Therefore, the present invention is directed to improving SAP absorption rate and permeability performance, without adversely affecting other fluid absorption and retention properties of the SAP particles, by the addition of clay during the manufacturing process.

SUMMARY

The present invention is directed to SAP particles and methods of manufacturing superabsorbent polymer containing clay. More particularly, the present invention is directed to SAP containing clay comprising a water-absorbing resin and clay, and a method of manufacturing such SAP-clay particles.

An embodiment of the present invention comprises a process for the production of superabsorbent polymer containing clay and particles thereof based on a process for the preparation of superabsorbent polymer comprising the steps of:

(I) polymerizing a polymerization mixture comprising: (a) one or more ethylenically unsaturated carboxyl-containing monomers, (b) one or more crosslinking agents, (c) optionally one or more comonomers copolymerizable with the carboxyl-containing monomer, (d) neutralizing agent to partially neutralize the polymer to from about 50% to about 99%, by weight, and (e) a polymerization medium, to form a crosslinked partially neutralized hydrogel, (II) admixing clay with the crosslinked partially neutralized hydrogel to form partially neutralized superabsorbent polymer-clay hydrogel;

(III) drying the crosslinked partially neutralized hydrogel at a temperature from about 190° C. to about 210° C. and for a time period of from about 15 minutes to about 120 minutes, and (IV) comminuting the dried partially neutralized superabsorbent polymer-clay hydrogel to particles.

An embodiment of the present invention includes the preparation of superabsorbent polymer containing clay wherein the superabsorbent polymer is present in an amount of about 90% to about 99.5%, by weight, and the clay is present in an amount of about 10% to about 0.5%, by weight.

Another embodiment of the present invention further includes grinding the superabsorbent polymer containing clay hydrogel into superabsorbent polymer particulate having a particle size from about 150 μm to about 850 μm as measured by screening through a U.S. standard 20 mesh screen and retained on a U.S. standard 100 mesh screen.

An embodiment of the present invention further includes a superabsorbent polymer particulate made by the foregoing process. In addition, the present invention is directed to absorbent compositions or sanitary articles such as diapers that may contain superabsorbent polymer compositions of the present invention.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects, and advantages of the present invention will become better understood with regard to the following description, appended claims, and accompanying drawings where:

FIG. 1 is a side view of the test apparatus employed for the Free Swell Gel Bed Permeability Test;

FIG. 2 is a cross-sectional side view of a cylinder/cup assembly employed in the Free Swell Gel Bed Permeability Test apparatus shown in FIG. 1;

FIG. 3 is a top view of a plunger employed in the Free Swell Gel Bed Permeability Test apparatus shown in FIG. 1; and FIG. 4 is a side view of the test apparatus employed for the Absorbency Under Load Test.

DEFINITIONS

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices that can absorb and contain fluids. For example, personal care absorbent articles refer to devices that are placed against or near the skin to absorb and contain the various fluids discharged from the body.

The term "cross linked" used in reference to the superabsorbent polymer refers to any means for effectively rendering normally water-soluble materials substantially water-insoluble but swellable. Such a cross linking means can include, for example, physical entanglement, crystalline domains, covalent bonds, ionic complexes and associations, hydrophilic associations such as hydrogen bonding, hydrophobic associations, or Van der Waals forces.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "dry superabsorbent polymer composition" generally refers to the superabsorbent polymer composition having less than about 10% moisture.

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the samples by weight are measured as more than 2 microns.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod-like, polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "superabsorbent materials" refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" refers to a superabsorbent polymer comprising a surface additive in accordance with the present invention.

The terms "superabsorbent polymer" and "superabsorbent polymer preproduct" refer to a material that is produced by conducting all of the steps for making a superabsorbent polymer as described herein, up to and including drying the material, and coarse grinding in a crusher.

The terms "superabsorbent polymer containing clay" and "superabsorbent polymer-clay" and "SAP-clay" will be used throughout to represent superabsorbent polymer containing clay as set forth in the present application.

The term "surface cross linking" means that the level of functional cross links in the vicinity of the surface of the superabsorbent polymer particle generally is higher than the level of functional cross links in the interior of the superabsorbent polymer particle. As used herein, "surface" describes the outer-facing boundaries of the particle. For porous superabsorbent polymer particles, exposed internal surfaces also are included in the definition of surface.

The term "thermoplastic" describes a material that softens when exposed to heat and which substantially returns to a non-softened condition when cooled to room temperature.

The term "% by weight" or "% wt" when used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

An embodiment of the present invention comprises a process for the production of superabsorbent polymer containing clay based on a process for the preparation of superabsorbent polymer containing clay comprising the steps of:
(I) polymerizing a polymerization mixture comprising: (a) one or more ethylenically unsaturated carboxyl-containing monomers, (b) one or more crosslinking agents, (c) optionally, one or more comonomers copolymerizable with the carboxyl-containing monomer, (d) neutralizing agent to partially neutralize the polymer to from about 50% to about 99%, by weight, and (e) a polymerization medium, to form a crosslinked partially neutralized hydrogel,
(II) admixing clay with the crosslinked partially neutralized hydrogel to form partially neutralized superabsorbent polymer-clay hydrogel;
(III) drying the crosslinked partially neutralized hydrogel at a temperature from about 190° C. to about 210° C. and for a time period of from about 15 minutes to about 120 minutes, and
(IV) comminuting the dried partially neutralized superabsorbent polymer-clay hydrogel to particles.

The SAP component of the SAP-clay particles is prepared by well-known continuous and discontinuous processes. The monomers comprising the SAP component of the SAP-clay particles typically are polymerized in aqueous solution to form an SAP hydrogel. However, the SAP component of the present particles may be prepared by any other method known to persons skilled in the art, like inverse suspension polymerization.

A superabsorbent polymer as set forth in the embodiments of the present invention is obtained by the initial polymerization of from about 55% to about 99.9% by weight of the superabsorbent polymer of polymerizable unsaturated acid group containing monomer. A suitable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75% by weight of the acid groups to be carboxyl groups.

The acid groups are neutralized to the extent of at least about 25 mol %, that is, the acid groups are desirably present as sodium, potassium, or ammonium salts. In some aspects, the degree of neutralization may be at least about 50 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal cross linking agents.

In some aspects, the suitable monomer that can be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer of the invention also includes internal cross linking agents. The internal cross linking agent has at least two ethylenically unsaturated double bonds, or one ethylenically unsaturated double bond and one functional group that is reactive toward acid groups of the polymerizable unsaturated acid group containing monomer, or several functional groups that are reactive towards acid groups can be used as the internal cross linking component and is desirably present during the polymerization of the polymerizable unsaturated acid group containing a monomer.

Examples of internal cross linking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri(meth)acrylates of butanediol or ethylene glycol, polyglycols or trimethylolpropane; di- and triacrylate esters of trimethylolpropane which may be oxyalkylated, desirably ethoxylated, with about 1 to about 30 moles of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl (meth)acrylate, alkoxylated allyl (meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of cross linking, such as N-methylol compounds of unsaturated amides, such as of methacrylamide or acrylamide, and the ethers derived there from. Ionic cross linkers such as multivalent metal salts may also be employed. Mixtures of the cross linking agents mentioned can also be employed. The content of the internal cross linking agents is from about 0.001% to about 5% by weight such as from about 0.2% to about 3% by weight based on the total amount of the polymerizable unsaturated acid group containing monomer.

In some aspects, initiators can be used for initiation of the free-radical polymerization. Suitable initiators include, but are not limited to, azo or peroxo compounds, redox systems or UV initiators, sensitizers, and/or radiation.

As previously noted, the polymerization reaction proceeds rapidly to yield a highly viscous hydrogel that is extruded, for example, onto a flat surface such as a continuously moving conveyor belt. The neutralized SAP hydrogel then is comminuted, and the clay is added to, typically as aqueous clay slurry, and intimately admixed with, the comminuted SAP hydrogel particles. The clay may also be added as solid particles, or a powder. The SAP hydrogel and clay components may then be intimately admixed, e.g., by extrusion, to disperse the clay in and on the hydrogel particles. The resulting neutralized SAP-clay mixture is then dried and sized, and optionally surface crosslinked to provide neutralized SAP-clay particles. Comminution of the SAP-clay hydrogel particles may be performed simultaneously or sequentially.

After comminutation, the viscous SAP-clay hydrogel particles are dehydrated (i.e., dried) to obtain SAP-clay particles in a solid or powder form. The dehydration step may be performed, for example, by heating the viscous SAP-clay hydrogel particles at a temperature of from about 190° C. to about 210° C. for about 15 minutes to about 120 minutes in a forced-air oven, or a time period of from about 15 minutes to about 110 minutes or from about 15 minutes to about 100 minutes, or from about 20 minutes to about 100 minutes. The dried SAP-clay hydrogel may then be subjected to further mechanical means for particle size reduction and classification including chopping, grinding, and sieving.

Such SAP-clay compositions may include superabsorbent polymer present in an amount of about 90% to about 99.5%, or from about 91% to about 99%, or from about 92% to about 98% by weight, and the clay is present in an amount of about 0.5% to about 10%, or from about 1 to about 9 wt %, or from about 2 to about 8 wt % by weight.

Clay Component

An embodiment of the present invention includes the preparation of superabsorbent polymer wherein the superabsorbent polymer is present in an amount of about 60% to about 90%, by weight, and the clay is present in an amount of about 0.5% to about 10%, by weight, or from about 1 to about 9 wt %, or from about 2 to about 8 wt %.

Clay useful in the present SAP-clay particles can be swelling or nonswelling clay. Swelling clays have the ability to absorb water and are swellable, layered organic materials. Suitable swelling clays include, but are not limited to, montmorillonite, saponite, nontronite, laponite, beidelite, hectorite, sauconite, stevensite, vermiculite, volkonskoite, magadite, medmontite, kenyaite, and mixtures thereof.

The swelling clay may be a smectite or vermiculite clay. More preferably, the clay is a smectite clay. Examples of suitable smectites include, but are not limited to, montmorillonite (often referred to as bentonite), beidelite, nontronite, hectorite, saponite, sauconite, and laponite. Bentonite is a naturally occurring combination of clay particles, rich in montmorillonite and also including other smectites, as well as nonclay mineral constituents.

Suitable nonswelling clays include, without limitation, kaolin minerals (including kaolinite, dickite, and nacrite), serpentine minerals, mica minerals (including illite), chlorite minerals, sepolite, palygorskite, bauxite, and mixtures thereof.

The clay also can be an organophilic clay. As used here and hereafter, the term "organophilic" is defined as the property of a compound to absorb at least its own weight, and preferably many times its own weight, of an organic, water-immiscible compound. An organophilic compound optionally can absorb water or a water-miscible compound.

The terms "organophilic clay" and "organoclay" are used interchangeably herein to refer to various types of clay, e.g., smectites that have organoammonium ions substituted for metal cations (e.g., sodium and/or potassium) present between the clay layers. The term "organoammonium ion" refers to a substituted ammonium ion wherein one or more hydrogen atoms are replaced by an aliphatic or aromatic organic group. The organoclays, therefore, are solid compounds that have an inorganic component and an organic component.

Clay substrates of organophilic clay may include the smectite-type clays, particularly smectite-type clays that have a cation exchange capacity of at least 75 milliequivalents per 100 grams of clay. Useful clay substrates include, but are not limited to, the naturally occurring Wyoming variety of bentonite and similar clays, and hectorite, which is magnesium-lithium silicate clay. The clays may first be converted to the sodium form if they are not already in this form. This conversion can be effected by a cation exchange reaction using a soluble sodium compound by methods well known in the art. Smectite-type clays prepared synthetically also can be utilized, for example, montmorillonite, bentonite, beidelite, hectorte, saponite, and stevensite. Other useful clay substrates include nontronite, illite, attapulgite, and a fuller's earth.

Organoclays useful in the present invention also include those set forth in U.S. Pat. No. 2,531,427, wherein the organoclays cited in the '427 patent are incorporated herein by reference. These organoclays are modified clays that exhibit, in an inorganic liquid, some of the properties an untreated clay exhibits in water. For example, the ability to swell in organic liquids and form stable gels and colloidal dispersions is desirous.

Generally, the organoammonium ion substituted onto the clay substrate has an organic group that ranges from an aliphatic hydrocarbon moiety having 1 to 24 carbon atoms to an aromatic organic moiety, such as a benzyl group that can have a variety of groups substituted on the phenyl ring. The number of benzyl versus aliphatic hydrocarbon moieties substituted on the ammonium ion can vary from 3 to 0 aromatic moieties per aliphatic moiety (i.e., dimethyl dioctadecyl 0:2, methyl benzyl dioctadecyl 1:2, dibenzyl dioctabenzyl 2:2, tribenzyl octadecyl 3:1, and methyl dibenzyl octadecyl 2:1). The amount of organoammonium ion substituted onto the clay substrate typically is about 0.5% to about 50%, by weight of the organophilic clay.

Organoclays may comprise one or more of the following types of organoammonium cation-modified montmorillonite clays or benzyl organoclays, such as dimethyl benzyl (hydrogenated tallow) ammonium bentonite; methyl benzyl di(hydrogenated tallow) ammonium bentonite; and more generally organoammoniumcation modified montmorillonite clays.

The montmorillonite clays that can be so modified are the principal constituents of bentonite rock, and have the chemical compositions and characteristics described, for example, in Berry & Mason, "Mineralogy," pp. 508-509 (1959). Modified montmorillonite clays of this type (i.e., organoclays) are commercially available from Southern Clay Products, Inc., Gonzales, Tex., under trade designations such as CLAYTONE® 34 and 40, and from NL Industries, Inc., New York, N.Y., under trade designations such as BENTONE®. 27, 34, and 38. Other organoclays useful in the invention are the higher dialkyl dimethyl ammonium organoclays, such as dimethyl di-(hydrogenated tallow) ammonium bentonite; the benzyl ammonium organoclays, such as dimethyl benzyl (hydrogenated tallow) ammonium bentonite; and ethylhydroxy ammonium organoclays, such as methyl bis(2-hydroxyethyl) octadecyl ammonium bentonite. Examples of nonswelling organophilic clays are bentonite clays treated with an amine containing three to eight carbon atoms, e.g., propylamine, butylamine, or octylamine.

Other commercially available clays include ULTRAGLOSS® clays (hydrous kaolin) from BASF Corporation, Florham Park, N.J.; Purified Clay from Nanocor Technologies, Arlington Heights, Ill.; and HYDROGLOSS® from Huber, Atlanta, Ga.

Another suitable clay component comprises the aluminosilicates. Useful aluminosilicates are nonzeolite silicates wherein a portion of the silicon atoms are replaced by aluminum atoms. Because the aluminum atom has one positive nuclear charge less than the silicon atom, every aluminum atom replacing a silicon atom increases the negative charge of the lattice anion by one unit. Additional cations, therefore, are needed to neutralize the molecule. Consequently, in addition to aluminum atoms, aluminosilicates can include additional metal atoms, e.g., alkali and alkaline earth metal atoms, such as sodium, potassium, magnesium, calcium, iron, and zinc. Useful aluminosilicates have a layered structure. In accordance with the present invention, both naturally occurring and synthetic aluminosilicates are useful.

Naturally occurring aluminosilicates include the micas. Micas are infinite sheet silicates containing layers of tetrahedral. An example of a useful sheet-like aluminosilicate for the purposes of the invention is the synthetic aluminosilicate saponite. Synthetic saponite (CAS No. 1319-41-1) is commercially available as a white, odorless powder. Examples of useful naturally occurring micas are muscowite, biotite, phlogopite, lepidolite, zinnwaldite, paragonite, and montmorillonite.

A clay does not perform, like an SAP with respect to absorbing and retaining large amounts of an aqueous fluid. A clay typically is referred to, and considered, as a diluent for SAP particles in an attempt to improve one or more properties of the SAP. It also is expected that other SAP properties would be adversely affected by diluting an SAP with the clay. However, as demonstrated hereafter, after adding the clay to SAP particles, the beneficial properties associated with an SAP are diminished to a substantially lower degree than expected, while other beneficial properties are improved.

Surface Treatment

In embodiments wherein a surface crosslinking agent is used, the surface crosslinking agent is applied to the dried SAP particles. After application of the surface crosslinking agent, the SAP-clay particles are subjected to conditions wherein the surface crosslinking agent reacts with a portion of the carboxyl or amino groups of the SAP to crosslink the surfaces of the SAP particles. In general, surface cross linking is a process that is believed to increase the cross link density of the polymer matrix in the vicinity of the superabsorbent polymer particle surface with respect to the cross linking density of the particle interior.

In some particular aspects, desirable surface cross linking agents include chemicals with one or more functional groups that are reactive toward pendant groups of the polymer chains, typically the acid groups. The surface cross linking agent may be present in an amount of from about 0.001% to about 5% by weight of the dry superabsorbent polymer composition, and such as from about 0.1% to about 3% by weight, and such as from about 0.1% to about 1% by weight, based on the weight of the dry superabsorbent polymer composition. Applicants have found that a heat treatment step after addition of the surface cross linking agent is desirable.

In one particular aspect, the particulate superabsorbent polymer may be coated or surface-treated with an alkylene carbonate followed by heating to affect surface cross linking, which can improve the surface cross linking density and the gel strength characteristics of the superabsorbent polymer composition particle. More specifically, the surface cross linking agent is coated onto the superabsorbent polymer particulate by mixing the polymer particulate with an aqueous alcoholic solution of the alkylene carbonate surface cross linking agent. The amount of alcohol is determined by the solubility of the alkylene carbonate and is kept as low as possible for various reasons. Suitable alcohols may include methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer composition. In other aspects, the alkylene carbonate surface cross linking agent is dissolved in water without any alcohol. In still other aspects, the alkylene carbonate surface cross linking agent may be applied from a powder mixture, for example, with an inorganic carrier material, such as silicone dioxide ($SiO_2$), or in a vapor state by sublimation of the alkylene carbonate.

To achieve the desired surface cross linking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, that may follow the coating treatment, may be carried out as follows. In general, the heat treatment is at a temperature of from about 100° C. to about 300° C. Lower temperatures are possible if highly reactive epoxide cross linking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface cross-linking properties. The thermal treatment may be carried out in conventional dryers or ovens known in the art.

In some aspects, the superabsorbent polymer composition of the present invention may include from 0% to about 5% by weight, or from about 0.001% to about 5% by weight, or from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, the Applicants have found that maleated polypropylene to be a desirable thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), poly(diallyldimethyl ammonium chloride). Poly(vinyl amines) include, but are not limited to, LUPAMIN® 9095 available from BASF Corporation, Mount Olive, N.J. Examples of natural-based cationic polymers include, but are not limited to, partially deacetylated chitin, chitosan, and chitosan salts. Synthetic polypeptides such as polyasparagins, polylysines, polyglutamines, and polyarginines are also suitable cationic polymers.

The absorbent polymers according to the invention can comprise include from 0 to about 5 wt % of a multivalent metal salt, based on the weight of the mixture, on the surface of the polymer. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminum sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts can be employed.

The polymer and multivalent metal salt suitably are mixed by dry blending, or preferably in solution, using means well known to those skilled in the art. Aqueous solutions are preferred. With dry blending, a binder may be employed in an amount which sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The superabsorbent polymer compositions according to the invention may include from about 0.01% to about 2% by weight or from about 0.01% to about 1% by weight based on the dry superabsorbent polymer composition of a water-insoluble inorganic metal compound. The water-insoluble inorganic metal compound may include, but are not limited to, a cation selected from aluminum, titanium, calcium, or iron and an anion selected from phosphate, borate, or sulfate. Examples of water-insoluble inorganic metal compounds include aluminum phosphate and an insoluble metal borate. The inorganic metal compound may have a mass median particle size of less than about 2 μm, and may have a mass median particle size of less than about 1 μm.

The inorganic metal compound can be applied in the dry physical form to the surface of the superabsorbent polymer particles. For this, the superabsorbent polymer particles can be intimately mixed with the finely divided inorganic metal compound. The finely divided inorganic metal compound is usually added at about room temperature to the superabsorbent polymer particles and mixed in until a homogeneous mixture is present. For this purpose, mixing is effected in suitable mixers known in the art, such as fluidized bed mixers, paddle mixers, rotary drum mixers, or twin-worm mixers. The mixing of the SAP particles with the finely divided water-insoluble inorganic metal compound may take place before or after any surface cross linking, for example during the application of the surface cross linking agent.

Alternatively, a suspension of a finely divided water-insoluble inorganic metal compounds can be prepared and applied to a particulate SAP. The suspension is applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidal, viscosity modifiers, and other auxiliaries to assist in the preparation of the suspension. The suspension can be applied in conventional reaction mixers or mixing and drying systems as described above at a temperature in the range from room temperature to less than the boiling point of the dispersion medium, preferably at about room temperature. It is appropriate to combine the application of the suspension with a surface cross linking step by dispersing the finely divided water-insoluble metal salt in the solution of the surface cross linking agent. Alternatively, the suspension can also be applied before or after the surface cross linking step. The application of the slurry may be followed by a drying step.

In some aspects, the superabsorbent polymer compositions according to the invention can include from 0% to about 5%, or from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide is desirable. Products include SIPERNAT® 22S and AEROSIL® 200 available from Evonik Corporation, Parsippany, N.J. In some aspects, the particle diameter of the inorganic powder can be 1,000 μm or smaller, such as 100 μm or smaller.

In some aspects, the superabsorbent polymer compositions may also include from 0% to about 30% by weight of the dry superabsorbent polymer composition, such as from about 0.1% to about 5% by weight, of water-soluble polymers based by weight of the dry superabsorbent polymer composition, of partly or completely hydrolyzed polyvinyl acetate, polyvinylpyrrolidone, starch or starch derivatives, polyglycols, polyethylene oxides, polypropylene oxides, or polyacrylic acids.

In some aspects, additional surface additives may optionally be employed with the superabsorbent polymer particles, such as odor-binding substances, such as cyclodextrins, zeolites, inorganic or organic salts, and similar materials; anti-caking additives, flow modification agents, surfactants, viscosity modifiers, and the like. In addition, surface additives may be employed that perform several roles during surface modifications. For example, a single additive may be a surfactant, viscosity modifier, and may react to cross link polymer chains.

In some aspects, the superabsorbent polymer compositions of the present invention may be, after a heat treatment step, treated with water so that the superabsorbent polymer composition has water content of up to about 10% by weight of the superabsorbent polymer composition. This water may be added with one or more of the surface additives from above added to the superabsorbent polymer.

The superabsorbent polymer compositions according to the invention may be prepared either continuously or discontinuously in a large-scale industrial manner, the after-cross linking according to the invention being carried out accordingly. The partially neutralized monomer, such as acrylic acid, is converted into a gel by free-radical polymerization in aqueous solution in the presence of cross linking agents and any further components, and the gel is comminuted, dried, ground, and sieved off to the desired particle size. The superabsorbent polymer composition particles of the present invention generally include particle sizes ranging from about 150 to about 850 microns. The present invention may include at least about 40 wt % of the particles having a particle size from about 300 μm to about 600 μm, or at least about 50 wt % of the particles having a particle size from about 300 μm to about 600 μm, or at least about 60 wt % of the particles having a particle size from about 300 μm to about 600 μm as measured by screening through a U.S. standard 30 mesh screen and retained on a U.S. standard 50 mesh screen. In addition, the size distribution of the SAP particles of the present invention may include less than about 30% by weight of SAP particles having a size greater than about 600 microns, and less than about 30% by weight of SAP particles having a size of less than about 300 microns as measured using for example a RO-TAP® Mechanical Sieve Shaker Model B available from W. S. Tyler, Inc., Mentor Ohio.

It is well known to those skilled in the art that particle size distribution of the SAP particles resembles a normal distribution or a bell shaped curve. It is also known that for various reasons, the normal distribution of the particle size distribution may be skewed in either direction.

Surprisingly, it has been found that the absorption and retention properties of SAP particles may be improved by the addition of clay to a partially neutralized SAP hydrogel and drying the hydrogel-clay at elevated temperatures while maintaining the absorption under load at 0.9 psi properties. In particular, incorporating the resulting SAP-clay particles into a diaper core provides cores having improved fluid acquisition rates.

The superabsorbent polymer containing clay of the present invention exhibits certain characteristics, or properties, as measured by Free Swell Gel Bed Permeability (GBP), Centrifuge Retention Capacity (CRC), and absorbency under load at about 0.9 psi (AUL(0.9 psi)), and vortex time. The Free Swell Gel Bed Permeability (GBP) Test is a measurement of the permeability of a swollen bed of superabsorbent material in Darcy (e.g., separate from the absorbent structure) under a confining pressure after what is commonly referred to as "free swell" conditions. In this context, the term "free swell" means that the superabsorbent material is allowed to swell without a swell restraining load upon absorbing test solution as will be described. The Centrifuge Retention Capacity (CRC) Test measures the ability of the superabsorbent polymer composition to retain liquid therein after being saturated and subjected to centrifugation under controlled conditions. The resultant retention capacity is stated as grams of liquid retained per gram weight of the sample (g/g). The vortex time is a measure of the free swell absorbing rate of the polymer.

A superabsorbent polymer containing clay particulate made by a process of present invention may have a centrifuge retention capacity of from about 25 g/g to about 40 g/g, or from about 26 to about 30 g/g; and may have an absorption under load at 0.9 psi of from about 10 g/g to about 20 g/g, or from about 13 g/g to about 18 g/g, and a free swell gel bed permeability of from about 5 to about 100 Darcy, and a vortex time of about 70 seconds or less, or from about 30 to about 70 seconds.

The superabsorbent polymer containing clay according to the present invention can be employed in many products including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorbent layer without fluff content within the diaper construction, as a result of which particularly thin articles are possible. The polymers are furthermore suitable for use in hygiene articles (incontinence products) for adults.

The above test results show that the absorbent SAP-clay particles of the present invention can be used to absorb aqueous fluids. The fluid can be a body fluid, an industrial waste, or any other fluid that one desires to absorb. The absorbed fluid can be any water-containing fluid, and typically contains electrolytes, for example, urine, blood, saline, menses, and similar liquids.

The present SAP-clay particles, therefore, are useful in personal hygiene articles comprising: (A) a fluid-pervious top sheet; (B) a fluid-impervious back sheet; (C) a core positioned between (A) and (B), said core comprising: (C1) about 10 to 100% by weight of the SAP-clay particles of the present invention, and (C2) 0 to about 90% by weight of a fiber material; (D) optionally one or more tissue layers positioned directly above and/or below said core (C); and (E) optionally an acquisition layer positioned between (A) and (C).

The fluid-pervious top sheet (A) is the layer which is in direct contact with the skin of the wearer. Top sheet (A) generally comprises synthetic or cellulosic fibers or films, i.e., polyesters, polyolefins, rayon, or natural fibers, such as cotton. In the case of nonwoven materials, the fibers generally are joined together by binders such as a polyacrylate. Preferred materials are polyesters, rayon and blends thereof, polyethylene, and polypropylene. The fluid-impervious layer (B) is generally a sheet of polyethylene or polypropylene.

The core (C) includes SAP-clay particles (C1) of the present invention, and also can include a fiber material (C2). Fiber material (C2) typically is hydrophilic, i.e., aqueous fluids are rapidly distributed across the fibers. The fiber material typically is cellulose, modified cellulose, rayon, or polyester, such as polyethylene terephthalate. Preferred fibers are cellulose fibers, such as pulp. The fibers may have a diameter of about 1 to about 200 μm, or about 10 to about 100 μm, and a minimum length of about 1 mm.

The amount of fiber material (C2) based on the total weight of the core is typically about 20% to about 80% by weight, or about 40% to about 70% by total weight of C(1) and C(2). Core (C) typically also can be a heavily loaded core (e.g., 60-95 wt % SAP-clay particles/5-40 wt % fluff).

The SAP-clay particles often are present in core (C) as a pressed sheet containing the particles, and optionally fluff and/or nonwoven fibers. A single absorbent layer or sheet containing SAP-clay particles of the present invention can be used as the absorbent component of a core (C). A plurality of absorbent layers or sheets may be used in the core (C), together with a wicking layer (e.g., a tissue layer) between absorbent layers or sheets to provide improved wicking of a fluid between and through the absorbent sheets. In other embodiments, at least one of the absorbent layers or sheets in a core (C) contains nonwoven fibers to improve wet strength of the absorbent core and assist in wicking.

A core (C) may contain two to five absorbent layers or sheets. By utilizing a laminate of thin absorbent layers or sheets, as opposed to a single, thicker absorbent layer or sheet, horizontal expansion of the core is decreased, and vertical expansion is promoted. This feature provides a good fluid transport through the core, provides a better fitting diaper after an initial insult, and avoids leaking when the diaper is subsequently rewet by a second and additional insult. In more preferred embodiments, core (C) contains a laminate of two or more absorbent layers or sheets of SAP-clay particles wherein a wicking layer is positioned between each absorbent sheet layer or sheet, and on top and at the bottom of the laminate.

An absorbent layer or sheet containing SAP-clay particles of the present invention, or a laminate comprising such layers or sheets, is present in an absorbent core to provide a desired basis weight (i.e., weight of SAP in the core) of about 50 to about 800 gsm (grams/square meter), or from about 150 to about 600 gsm. To achieve the full advantage of the present invention, the basis weight is from about 300 to about 550 gsm. The desired basis weight of the core is related to the end use of the core. For example, diapers for newborns have a low basis weight, as opposed to a medium basis weight for toddlers, and a high basis weight for overnight diapers.

In another embodiment, a present diaper core may include a topsheet (A), a core (C), and a backsheet (B), i.e., an acquisition layer is not present. An example of a topsheet (A) is staple length polypropylene fibers having a denier of about 1.5, such as Hercules-type 151 polypropylene marketed by Hercules, Inc., Wilmington, Del. As used herein, the term "staple length fibers" refers to having a length of at least about 15.9 mm (0.62 inches). The back sheet (B) is impervious to liquids, and typically is manufactured from a thin plastic film, although other flexible liquid impervious materials also can be used. The back sheet prevents exudates absorbed and contained in the absorbent core (C) from wetting articles, such as bed sheets and undergarments, that contact the diaper.

For an absorbent article having a core (C) containing a "fluff" component, the "fluff" comprises a fibrous material in the form of a web or matrix. Fibers include naturally occurring fibers (modified or unmodified). Examples of suitable unmodified/modified naturally occurring fibers include cotton, Esparto grass, bagasse, kemp, flax, silk, wool, wood pulp, chemically modified wood pulp, and jute.

The cores also can include an optional nonwoven fiber, for example, polypropylene, polyethylene, polyethylene terephthalate, viscose, and mixtures thereof. Also, an open fiber mesh of nonwoven fibers can be used, for example, cellulose acetate fiber. Nonwoven fibers can be made by drylaid thermobonded, carded air-through bonded, spunbond, or spun-meltblown-spun processes. Nonwoven fibers impart additional wet strength to an absorbent layer or sheet when used in an amount of about 10 to about 20 grams per square meter (gsm) of sheet material.

Suitable fibers, and fiber meshes, can be made from polyvinyl chloride, polyvinyl fluoride, polytetrafluoroethylene, polyvinylidene chloride, polyacrylics such as ORLON®, polyvinyl acetate, polyethylvinyl acetate, nonsoluble or soluble polyvinyl alcohol, polyolefins such as polyethylene (e.g., PULPEX®) and polypropylene, polyamides (e.g., nylon), polyesters (e.g., DACRON® or KODEL®), polyurethanes, polystyrenes, and the like.

Hydrophilic fibers are preferred, and include rayon, polyester fibers, such as polyethylene terephthalate (e.g., DACRON®), hydrophilic nylon (e.g., HYDROFIL®), and the like. Suitable hydrophilic fibers can also be obtained by hydrophilizing hydrophobic fibers, such as surfactant-treated or silica-treated thermoplastic fibers derived from, for example, polyolefins, such as polyethylene or polypropylene, polyacrylics, polyamides, polystyrenes, polyurethanes, and the like.

The improved results demonstrated by a core containing SAP-clay particles of the present invention permit the thickness of the core to be reduced. Typically, cores contain 50% or more fluff or pulp to achieve rapid liquid absorption while avoiding problems like gel blocking. The present cores, which contain SAP-clay particles acquire liquids sufficiently fast to avoid problems, like gel blocking, and, therefore, the amount of fluff or pulp in the core can be reduced, or eliminated. A reduction in the amount of the low-density fluff results in a thinner core, and, accordingly, a thinner diaper. Therefore, a core of the present invention can contain at least 50% SAP-clay particles, preferably at least 60%, and up to 80% of the SAP-clay particles. In various embodiments, the presence of a fluff is no longer necessary, or desired.

The superabsorbent polymer containing clay according to the invention may also be employed in absorbent articles that are suitable for further uses. In particular, the superabsorbent polymer compositions of this invention can be used in absorbent compositions for absorbents for water or aqueous liquids, desirably in constructions for absorption of body fluids, in foamed and non-foamed sheet-like structures, in packaging materials, in constructions for plant growing, as soil improvement agents, or as active compound carriers. For this, they are processed into a web by mixing with paper or fluff or synthetic fibers or by distributing the superabsorbent polymer composition particles between substrates of paper, fluff, or non-woven textiles, or by processing into carrier materials. They are further suited for use in absorbent compositions such as wound dressings, packaging, agricultural absorbents, food trays and pads, and the like.

The present invention may be better understood with reference to the following examples.

Test Procedures

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles that are pre-screened through a U.S. standard 30-mesh screen and retained on a U.S. standard 50-mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at about 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 290 g force with a variance from about 280 to about 300 g force), for 3 minutes. G force is defined as a unit of inertial force on a body that is subjected to rapid acceleration or gravity, equal to 32 ft/sec$^2$ at sea level. The bags are removed and weighed, with the empty bags (controls) being weighed first, followed by the bags containing the superabsorbent polymer composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

sample/bag after centrifuge−empty bag after centrifuge−dry sample weight/dry sample weight The three samples are tested, and the results are averaged to determine the Centrifuge Retention Capacity (CRC) of the superabsorbent polymer composition.

Free-Swell Gel Bed Permeability Test (FSGBP)

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2 and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm$^2$ (2.07 kPa), over a sample area of about 28.27 cm.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The superabsorbent polymer particles can be prescreened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will prevent liquid in the sample container from being released onto a flat surface due to surface tension. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in $cm^2$ is obtained by the following equation: $K=[Q*H*\mu]/[A*\rho*P]$, where K=Permeability ($cm^2$), Q=flow rate (g/sec), H=height of swollen sample (cm), $\mu$=liquid viscosity (poise) (approximately one centipoise for the test solution used with this Test), A=cross-sectional area for liquid flow (28.27 $cm^2$ for the sample container used with this Test), $\rho$=liquid density (g/$cm^3$) (approximately one g/$cm^3$, for the test solution used with this Test) and P=hydrostatic pressure (dynes/$cm^2$) (normally approximately 7,797 dynes/$cm^2$). The hydrostatic pressure is calculated from $P=\rho*g*h$, where $\rho$=liquid density (g/$cm^3$), g=gravitational acceleration, nominally 981 cm/$sec^2$, and h=fluid height, e.g., 7.95 cm for the Gel Bed Permeability Test described herein.

A minimum of two samples is tested and the results are averaged to determine the gel bed permeability of the sample.

Absorbency Under Load (AUL0.9 psi) Test

The Absorbency Under Load (AUL) Test measures the ability of the superabsorbent polymer composition particles to absorb a 0.9 weight percent solution of sodium chloride in distilled water at room temperature (test solution) while the material is under a load of 0.9 psi. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9"(22.9 cm×22.9 cm), with a depth of 0.5 to 1"(1.3 cm to 2.5 cm) is commonly used for this test method.

A 12.5 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 12.5 cm diameter filter paper circles.

A supply of saline (0.9% sodium chloride in distilled water, by weight).

Referring to FIG. 4, the cylinder 412 of the AUL assembly 400 used to contain the superabsorbent polymer composition particles 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch(2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition particles in the bottom of the cylinder is recorded as 'SA,' for use in the AUL calculation described below. Care is taken to be sure no superabsorbent polymer particles cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the superabsorbent polymer composition particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9\ psi) = (B-A)/SA$$

wherein

A=Weight of AUL Unit with dry SAP

B=Weight of AUL Unit with SAP after 60 minutes absorption

SA=Actual SAP weight

A minimum of two tests is performed and the results are averaged to determine the AUL value under 0.9 psi load. The samples are tested at about 23° C. and about 50% relative humidity.

Vortex Time Test

The vortex test measures the amount of time in seconds required for 2 grams of a superabsorbent material to close a vortex created by stirring 50 milliliters of saline solution at 600 revolutions per minute on a magnetic stir plate. The time it takes for the vortex to close is an indication of the free swell absorbing rate of the superabsorbent material.

Equipment and Materials

1. Schott Duran 100 ml Beaker and 50 ml graduated cylinder.
2. Programmable magnetic stir plate, capable of providing 600 revolutions per minute (such as that commercially available from PMC Industries, under the trade designation Dataplate® Model #721).
3. Magnetic stir bar without rings, 7.9 millimeters.times.32 millimeters, Teflon® covered (such as that commercially available from Baxter Diagnostics, under the trade designation S/PRIM. brand single pack round stirring bars with removable pivot ring).
4. Stopwatch
5. Balance, accurate to ±0.01 g
6. Saline solution, 0.87 w/w % Blood Bank Saline available from Baxter Diagnostics (considered, for the purposes of this application to be the equivalent of 0.9 wt. % saline
7. Weighing paper
8. Room with standard condition atmosphere: Temp=23° C.±1° C. and Relative Humidity=50%±2%.

Test Procedure

1. Measure 50 ml±0.01 ml of saline solution into the 100 ml beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 g±0.01 g of the superabsorbent material to be tested on weighing paper. NOTE: The superabsorbent material is tested as received (i.e. as it would go into an absorbent composite such as those described herein). No screening to a specific particle size is done, though the particle size is known to have an effect on this test.
6. While the saline solution is being stirred, quickly pour the superabsorbent material to be tested into the saline solution and start the stopwatch. The superabsorbent material to be tested should be added to the saline solution between the center of the vortex and the side of the beaker.
7. Stop the stopwatch when the surface of the saline solution becomes flat and record the time.
8. The time, recorded in seconds, is reported as the Vortex Time.

EXAMPLES

The following examples and are provided to illustrate the invention and do not limit the scope of the claims. Unless otherwise stated all parts, and percentages are by weight.

Preproduct [A Typical Preparative Procedure]

Into a polyethylene vessel equipped with an agitator and cooling coils was added, 25.0 kg of 50% NaOH to 37 kg of distilled water and cooled to 20° C. 9.6 kg of glacial acrylic acid was then added to the caustic solution and the solution again cooled to 20° C. 47.8 g of polyethylene glycol monoallylether acrylate, 47.8 g of ethoxylated trimethylol propane triacrylate SARTOMER® 454 product, and 19.2 kg of glacial acrylic acid were added to the first solution, followed by cooling to 4-6° C. Nitrogen was bubbled through the monomer solution for about 10 minutes. The monomer solution was then discharged in 7.7 kg batches into rectangular trays. To each batch 80 g of 1% by weight of $H_2O_2$ aqueous solution, 120 g of 2 wt % aqueous sodium persulfate solution, and 72 g of 0.5 wt % aqueous sodium erythorbate solution was added homogeneously into the monomer solution stream by injection of the sodium erythorbate solution into the stream of the monomer solution being conveyed from the monomer tank into a tray. The initiated monomer was allowed to polymerize for 20 minutes. The resulting hydrogel was chopped and extruded with a Hobart 4M6 commercial extruder, followed by drying in a Procter & Schwartz Model 062 forced air oven at 195° C. for 12 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm.

Comparative Examples 1-6

For the Comparative Examples 1-6 set forth herein, the Kaolin clay was added to the extruded gel by the aid of a nozzle and kneaded well before drying.

TABLE 1

Base Polymer Dried at 185° C. for 18 minutes

|  | Kaolin Clay % | CRC | Vortex Sec |
|---|---|---|---|
| Comp Ex 1 | 0 | 32.2 | 40 |
| Comp Ex 2 | 2 | 30.05 | 35 |
| Comp Ex 3 | 3 | 29.8 | 36 |
| Comp Ex 4 | 4 | 29.1 | 34 |
| Comp Ex 5 | 5 | 28.4 | 33 |
| Comp Ex 6 | 10 | 26.5 | 30 |

Comparative Examples 7-12

The Preproduct was coated in an Anvil MIX9180 mixer with 1% ethylene carbonate, 4% water, and 350 ppm Chemcor 43G40SP (available from Chemcor Corporation, Chester, N.Y.) maleated polypropylene based on the dry superabsorbent polymer composition weight. The coated superabsorbent polymer was heat treated to about 195° C. for about 40 minutes residence time in order to effectuate the surface crosslinking of the polymer particles.

TABLE 2

Examples from Table 1 after Surface Crosslinking

|  | Kaolin Clay % | CRC g/g | Vortex Sec | AUL(0.9 psi) g/g |
|---|---|---|---|---|
| Comp Ex 7 | 0 | 27.5 | 85 | 14.5 |
| Comp Ex 8 | 2 | 27.1 | 36 | 15.1 |
| Comp Ex 9 | 3 | 26.45 | 31 | 14.85 |
| Comp Ex 10 | 4 | 25.13 | 32 | 16.6 |
| Comp Ex 11 | 5 | 24.1 | 33 | 14.85 |
| Comp Ex 12 | 10 | 23.3 | 31 | 14.85 |

Comparative Examples 13 & 14

Examples 1-10

TABLE 3

Base Polymer Dried at 195° C. for 18 minutes

|  | Kaolin Clay % | CRC | Vortex Sec |
|---|---|---|---|
| Comp Ex 13 | 0 | 31.5 | 35 |
| 1 | 2 | 31.4 | 28 |
| 2 | 3 | 31 | 31 |
| 3 | 4 | 30.9 | 32 |
| 4 | 5 | 30.3 | 34 |
| 5 | 10 | 28.8 | 28 |

TABLE 4

Examples from Table 3 after Surface Crosslinking

|  | Kaolin Clay % | CRC g/g | Vortex Sec | AUL(0.9 psi) g/g |
|---|---|---|---|---|
| Comp Ex 14 | 0 | 27.9 | 94 | 14.2 |
| 6 | 2 | 27.7 | 39 | 14.8 |
| 7 | 3 | 27.4 | 40 | 14.5 |
| 8 | 4 | 26.6 | 40 | 17.3 |
| 9 | 5 | 27.2 | 33 | 13 |
| 10 | 10 | 26.2 | 33 | 15.6 |

Comparative Example 15 and Example 11

In Example 11, clay was added to the superabsorbent polymer hydrogel of the commercial product SXM9200 (SXM9200 is commercially available from Evonik Stockhausen, Greensboro N.C.) and dried at 195° C. for 18 minutes. Table 5 shows a comparison of SXM9200 without and with Kaolin clay. The properties of polymer stayed intact after ~4 wt % clay was added to the polymer. Also, as shown in Table 5, the results of the Vortex test improves with the addition of clay to the SXM9200 hydrogel (i.e., the polymer becomes faster under the Vortex test) and the permeability of the SAP—clay polymer, as measured by Free Swell Gel Bed Permeability, increases.

TABLE 5

SXM9200 with clay in hydrogel

|  | Bulk Density | CRC g/g | AUL (0.9 psi) g/g | Free Swell GBP | Vortex (sec) |
|---|---|---|---|---|---|
| Comp Ex 15 SXM9200 | 0.58 | 30.43 | 12.62 | 5 | 89 |
| Ex 11 | 0.60 | 29.96 | 14.49 | 29.6 | 32 |

Comparative Example 16 and Example 12—Diapers

Diapers were constructed using 45% SAP structure wherein the SAP was one of 1) SXM9200, 2) SXM9200 including Kaolin clay in the polymer. SXM9200 is commercially available from Evonik Stockhausen, Inc., Greensboro, N.C. Construction for all diaper cores were a 600 GSM core and density of 0.13 with a homogenous blend of SAP and pulp with a light pulp dusting layer. Target weight specifications were achieved and maintained within normal production variability. Each core was assembled using a poly back sheet, 18 GSM hydrophilic top sheet and 30 GSM SBPP ADL.

A weighted (3.6 Kg) 4"×4" block is placed on the flat diaper core 2.5 cm forward of the diaper core centerline; resulting in a test pressure of 0.5 PSI. The article was insulted with 80 ml of saline and allowed to penetrate into the diaper core. Record acquisition time. The weighted block was allowed to remain on the diaper core for a period of 5 minutes. After 5 minutes period, the block is removed. Rewet is measured by placing a pre-weighed stack of 9.0 cm filter paper over the insult point and applying a weight of 2.2 kg. After 2 minutes remove the weight, weigh filter paper and record the rewet values. The test was repeated for a total of 3 acquisitions. If the diaper core at any time fails to acquire the liquid volume within the 5 minutes allowed, the test is stopped and recorded as such.

TABLE 6

Diaper Testing Results

| | Acquisition Time (Sec) | | | Rewet (grams) | | |
|---|---|---|---|---|---|---|
| | Insult #1 | Insult #2 | Insult #3 | Insult #1 | Insult #2 | Insult #3 |
| Comp Ex 16 (Without Clay) | 98 | 208 | 248 | 0.1 | 5.4 | 12.6 |
| Example 12 (With Clay) | 81 | 153 | 186 | 0.1 | 5 | 10.4 |

As shown in Table 6, the addition of the clay to the hydrogel according to the conditions of the invention provides adequate time of fluid in the diaper.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed:

1. A superabsorbent polymer containing clay particulate comprising:
    a) a superabsorbent polymer particulate comprising an intimately admixed blend of from about 90 wt % to about 99.5 wt % of a superabsorbent polymer hydrogel and from about 0.5 wt % to about 10 wt % of a clay; wherein the admixed blend is dried and comminuted into superabsorbent polymer particulate;
    b) wherein the superabsorbent polymer particulate of a) is surface treated with from about 0.001 wt % to about 5 wt % of a surface crosslinking agent to form a surface crosslinked superabsorbent polymer particulate;
    c) wherein the surface crosslinked particulate composition of b) is surface treated with from about 0.01 wt % to about 5 wt % of a multivalent salt to form the superabsorbent polymer containing clay particulate;
    d) wherein the superabsorbent polymer particulate composition of b), c), or b) and c) is further surface treated with from about 0.01 wt % to about 5 wt % of a cationic polymer; and
    wherein the superabsorbent polymer containing clay particulate has a free swell gel bed permeability of at least about 10 Darcy, as measured by the Free Swell Gel Bed Permeability Test.

2. The superabsorbent polymer containing clay particulate of claim 1 wherein at least about 40% by weight of the superabsorbent polymer particulate have a particle size from about 300 μm to about 600 μm as measured by screening through a U.S. standard 30 mesh screen and retained on a U.S. standard 50 mesh screen.

3. The superabsorbent polymer containing clay particulate of claim 1 further comprising e) from about 0.01 wt % to about 0.5 wt % of a thermoplastic polymer.

4. The superabsorbent polymer containing clay particulate of claim 1 wherein the clay comprises a kaolin mineral.

5. The superabsorbent polymer containing clay particulate of claim 1 having a centrifuge retention capacity of from about 25 g/g to about 40 g/g as measured by the Centrifuge Retention Capacity Test.

6. The superabsorbent polymer containing clay particulate of claim 1 having an absorption under load at 0.9 psi of from about 10 g/g to about 20 g/g as measured by the Absorbency Under Load (AUL0.9 psi) Test.

7. The superabsorbent polymer containing clay particulate of claim 1 having a free swell gel bed permeability of from about 10 Darcy to about 100 Darcy as measured by the Free Swell Gel Bed Permeability Test.

8. The superabsorbent polymer containing clay particulate of claim 1 having a vortex time of less than about 70 seconds.

9. An absorbent composition comprising the superabsorbent polymer containing clay particulate of claim 1.

10. A sanitary article comprising the superabsorbent polymer containing clay particulate of claim 1.

11. A diaper comprising the superabsorbent polymer containing clay particulate of claim 1.

12. A diaper having a core, said core comprising at least 10% by weight of the superabsorbent polymer containing clay particulate of claim 1.

13. The diaper of claim 12 wherein the core comprises 20-80% by weight of the superabsorbent polymer containing clay particulate.

14. The diaper of claim 12 further comprising a topsheet in contact with a first surface of the core, and a backsheet in contact with a second surface of the core, said second core surface opposite from said first core surface.

15. The diaper of claim 14 further comprising an acquisition layer disposed between the topsheet and the core.

16. The superabsorbent polymer containing clay particulate of claim 1, wherein said cationic polymer comprises poly(vinyl amine).

17. The superabsorbent polymer containing clay particulate of claim 1, wherein said superabsorbent polymer containing clay particulate has a water content of up to about 10% by weight.

* * * * *